(12) United States Patent
Hsia

(10) Patent No.: US 11,872,252 B2
(45) Date of Patent: Jan. 16, 2024

(54) COMPOSITIONS AND METHODS FOR TREATING VIRAL INFECTION

(71) Applicant: Houn Simon Hsia, Tustin, CA (US)

(72) Inventor: Houn Simon Hsia, Tustin, CA (US)

( * ) Notice: Subject to any disclaimer, the term of this patent is extended or adjusted under 35 U.S.C. 154(b) by 0 days.

(21) Appl. No.: 18/019,979

(22) PCT Filed: Aug. 10, 2021

(86) PCT No.: PCT/US2021/045399
§ 371 (c)(1),
(2) Date: Feb. 6, 2023

(87) PCT Pub. No.: WO2022/035869
PCT Pub. Date: Feb. 17, 2022

(65) Prior Publication Data
US 2023/0285471 A1 Sep. 14, 2023

Related U.S. Application Data

(60) Provisional application No. 63/063,542, filed on Aug. 10, 2020.

(51) Int. Cl.
| | |
|---|---|
| *A61K 33/00* | (2006.01) |
| *A61K 35/60* | (2006.01) |
| *A61P 31/14* | (2006.01) |
| *A61K 31/122* | (2006.01) |
| *A61K 33/04* | (2006.01) |
| *A61K 36/064* | (2006.01) |
| *A61K 45/06* | (2006.01) |
| *A61N 5/10* | (2006.01) |

(52) U.S. Cl.
CPC .............. *A61K 35/60* (2013.01); *A61K 31/122* (2013.01); *A61K 33/04* (2013.01); *A61K 36/064* (2013.01); *A61K 45/06* (2013.01); *A61N 5/10* (2013.01); *A61P 31/14* (2018.01)

(58) Field of Classification Search
CPC ................................ A61K 31/00; A61K 33/24
See application file for complete search history.

(56) References Cited

U.S. PATENT DOCUMENTS

2006/0078629 A1    4/2006    Serfontein

OTHER PUBLICATIONS

Martindale et al., "Nutrition therapy in critically ill patients with Coronavirus Disease 2019", Journal of Parenteral and Enteral Nutrition, 44(7):1174-1184, Jul. 12, 2020.*
Guillin, et al. "Selenium, Selenoproteins and Viral Infection," CIRI, Centre International de Recherche en Infectiologie, CIRI, 69007 Lyon, France. 64 pages.

(Continued)

Primary Examiner — Rosanne Kosson
(74) Attorney, Agent, or Firm — Fish IP Law, LLP

(57) ABSTRACT

Compositions and methods are provided in which a nutritional supplement that is utilized in the treatment viral infections (e.g., coronavirus, HCV, HIV), by correcting dysregulation of apoptosis, reducing production of pro-inflamatory cytokines, and increasing production of host anti-viral compounds. The nutritional supplements can be used in combination with known antiviral therapies, as well as low level radiotherapy and/or chemotherapy drugs conventionally used in the treatment of neoplastic disease.

19 Claims, 17 Drawing Sheets

(56) References Cited

OTHER PUBLICATIONS

Kieliszek, et al. "Selenium supplementation in the prevention of coronavirus infections (COVID-19)," ScienceDirect, vol. 143, Oct. 2020. 9 pages.

Wang, H. et al., "Reduction of Splenic Immunosuppressive Cells and Enhancement of Anti-Tumor Immunity by Synergy of Fish Oil and Selenium Yeast". PLOS ONE, Jan. 2013, vol. 8, No. I.article No. e52912, pp. 1-11.

\* cited by examiner

COMPOSITIONS AND METHODS FOR TREATING VIRAL INFECTION

This application claims priority to U.S. Provisional Patent Application No. 63/063,542 filed on Aug. 10, 2020. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is compositions and methods for treating viral infections, in particular coronavirus infections.

BACKGROUND

The background description includes information that may be useful in understanding the present invention. It is not an admission that any of the information provided herein is prior art or relevant to the presently claimed invention, or that any publication specifically or implicitly referenced is prior art.

Coronaviruses are positive sense, single stranded, enveloped RNA viruses that have repeatedly crossed species barriers to cause disease in human and animals. In the past two decades, three novel human-pathogenic coronaviruses have emerged to cause epidemics of severe respiratory infection among human, including severe acute respiratory syndrome coronavirus (SARS-CoV) in 2003, Middle East respiratory syndrome coronavirus (MERS-CoV) since 2012, and most recently SARS-CoV-2 since December 2019. Infection with SARS-CoV-2 can result in a significant inflammatory response, particularly in the respiratory system, which can lead to death.

A number of existing drugs, such as remdesivir, chloroquine, hydroxychloroquine, nafamostat, camostat, and ivermectin, have been reported to exhibit anti-SARS-CoV-2 activity in vitro. Remdesivir is a nucleotide analog with broad-spectrum antiviral activity. Chloroquine and hydroxychloroquine are mildly immunosuppressive drugs used in the treatment of autoimmune diseases have been suggested for treatment of COVID-19, however recent studies indicate that they provide no apparent clinical benefit and may increase morbidity]. Nafamostat and camostat are a serine protease inhibitor used in the treatment of chronic pancreatitis and reflux esophagitis that are theorized to interfere with SARS-CoV-2 entry into cells, however data from well-designed randomized controlled trials for these drugs are not yet available Therefore, there is an urgent need to identify safe and effective approaches to the treatment of COVID-19.

SUMMARY OF THE INVENTION

The inventive subject matter provides compositions and methods in which a nutritional supplement is provided that is effective in treating viral infections (e.g., coronavirus, HCV, HIV), for example by correcting dysregulation of apoptosis, reducing production of pro-inflammatory cytokines, and increasing production of native anti-viral compounds (e.g., interferon). Such a nutritional supplement can be used in combination with known antiviral therapies (therapeutic antibodies, small molecule antiviral drugs), as well as low level radiotherapy and/or chemotherapy drugs conventionally used in the treatment of neoplastic disease (e.g., cancer).

One embodiment of the inventive concept is a method of treating an individual for a viral infection by obtaining a nutritional supplement that includes fish oil and selenium (e.g., in the form of selenium yeast), and administering the nutritional supplement to the individual in an amount effective to treat the viral infection or sequelae of the viral infection. The viral infection can result from infection with a virus that induces a dysregulation of apoptosis in a cell infected with the virus, where the nutritional supplement provides fish oil and selenium in quantities sufficient to modify an apoptic event in the cell infected with the virus upon administration. In some embodiments the amount of fish oil and selenium is also selected to reduce serum concentration of a pro-inflammatory cytokine. In some embodiments selenium is provided at from 1,000 µg to 10,000 µg per day, and/or fish oil at from 1,000 mg to 20 mg per day. The nutritional supplement can also include coenzyme Q10 (e.g., from 1 mg to 5,000 mg coenzyme Q10). In some embodiments the nutritional supplement can include three or more components listed in Table 1. Contemplated viral infections include those resulting from infection with a coronavirus (e.g., SARS-CoV-2), HCV, and/or HIV. Such treatment can be applied to an active infection, including asymptomatic infections. In other embodiments such treatment can be prophylactic. In some embodiments the nutritional supplement can be provided in combination with low-dose radiotherapy (e.g., a dose of up to 2 rems, provided as single or multiple doses) and/or a cancer chemotherapy drug (e.g., taxol, adriamycin, and avastin). Such a cancer chemotherapy drug can be provided at a low dose (e.g. from 1% to 50% or less) than dosages applied in treatment of cancer.

Another embodiment of the inventive concept is the use of a nutritional supplement that includes fish oil and selenium (e.g., in the form of selenium yeast), and administering the nutritional supplement to the individual in an amount effective to treat the viral infection or sequelae of the viral infection. The viral infection can result from infection with a virus that induces a dysregulation of apoptosis in a cell infected with the virus, where the nutritional supplement provides fish oil and selenium in quantities sufficient to modify an apoptic event in the cell infected with the virus upon administration. In some embodiments the amount of fish oil and selenium is also selected to reduce serum concentration of a pro-inflammatory cytokine. In some embodiments selenium is provided at from 1,000 µg to 10,000 µg per day, and/or fish oil at from 1,000 mg to 20 mg per day. The nutritional supplement can also include coenzyme Q10 (e.g., from 1 mg to 5,000 mg coenzyme Q10). In some embodiments the nutritional supplement can include three or more components listed in Table 1. Contemplated viral infections include those resulting from infection with a coronavirus (e.g., SARS-CoV-2), HCV, and/or HIV. Such treatment can be applied to an active infection, including asymptomatic infections. In other embodiments such treatment can be prophylactic. In some embodiments the nutritional supplement can be provided in combination with low-dose radiotherapy (e.g., a dose of up to 2 rems, provided as a single or multiple doses) and/or a cancer chemotherapy drug (e.g., taxol, adriamycin, and avastin). Such a cancer chemotherapy drug can be provided at a low dose (e.g. from 1% to 50% or less) than dosages applied in treatment of cancer.

Various objects, features, aspects and advantages of the inventive subject matter will become more apparent from the following detailed description of preferred embodiments, along with the accompanying drawing figures.

BRIEF DESCRIPTION OF THE DRAWINGS

FIG. 1 shows the effects of application of selenium and fish oil on BAX expression in cells with reduced apoptosis (in this instance, primary tumor cells).

FIG. 2 shows the effects of application of selenium and fish oil on BAX expression in cells with reduced apoptosis (in this instance, metastatic tumor cells).

FIG. 3 shows the effects of application of selenium and fish oil on Bcl-2 expression in cells with reduced apoptosis (in this instance, primary tumor cells).

FIG. 4 shows the effects of application of selenium and fish oil on Bcl-2 expression in cells with reduced apoptosis (in this instance, metastatic tumor cells).

FIG. 5 shows the effects of application of selenium and fish oil on caspase-3 expression in cells with reduced apoptosis (in this instance, tumor cells).

FIG. 6 shows the effects of application of selenium and fish oil on expression of protein markers associate with apoptosis (VEGF, p53, and HIF-α).

FIG. 7 shows the effects of application of selenium and fish oil on expression of caspase 8, which is associated with apoptosis.

FIG. 8 shows the effects of application of selenium and fish oil on expression of cytochrome C, which is associated with apoptosis.

FIG. 9 shows the effects of application of selenium, fish oil, and a combination of selenium and fish oil on the growth of tumor cells in culture, which can serve as an analog of certain virus-infected cells.

FIG. 10 shows the effects of application of selenium, fish oil, and a combination of selenium and fish oil on survival of tumor cells in culture, which can serve as an analog of certain virus-infected cells, as shown by staining with trypan blue.

FIG. 11 shows the effects of application of a nutritional supplement that includes selenium and fish oil on serum TNF-α concentration in an animal model of inflammation.

FIG. 12 shows the effects of application of a nutritional supplement that includes selenium and fish oil on serum IL-6 concentration in an animal model of inflammation.

FIG. 13 shows effects of application of a nutritional supplement that includes selenium and fish oil on expression of muscle-related proteins found in mitochondria and associated with inflammation (UCP3, UCP2) and an inflammation-related cytokine (IL6).

FIG. 14 shows effects of application of a nutritional supplement that includes selenium and fish oil on expression of VEGF.

FIG. 15 shows effects of application of a nutritional supplement that includes selenium and fish oil on expression of VEGF.

FIG. 16 shows effects of application of a nutritional supplement that includes selenium and fish oil on expression of TNF-α.

FIG. 17 shows effects of application of a nutritional supplement that includes selenium and fish oil on expression of TNF-α.

FIG. 18 shows effects of application of a nutritional supplement that includes selenium and fish oil on expression of IL-1β and IL-10.

FIG. 19 shows effects of application of a nutritional supplement that includes selenium and fish oil on expression of IL-1β.

FIG. 20 shows effects of application of a nutritional supplement that includes selenium and fish oil (N) on expression of IL2.

FIG. 21 shows effects of application of a nutritional supplement that includes selenium and fish oil (N) on expression of IL2 and IFN-γ.

DETAILED DESCRIPTION

Figure 1:
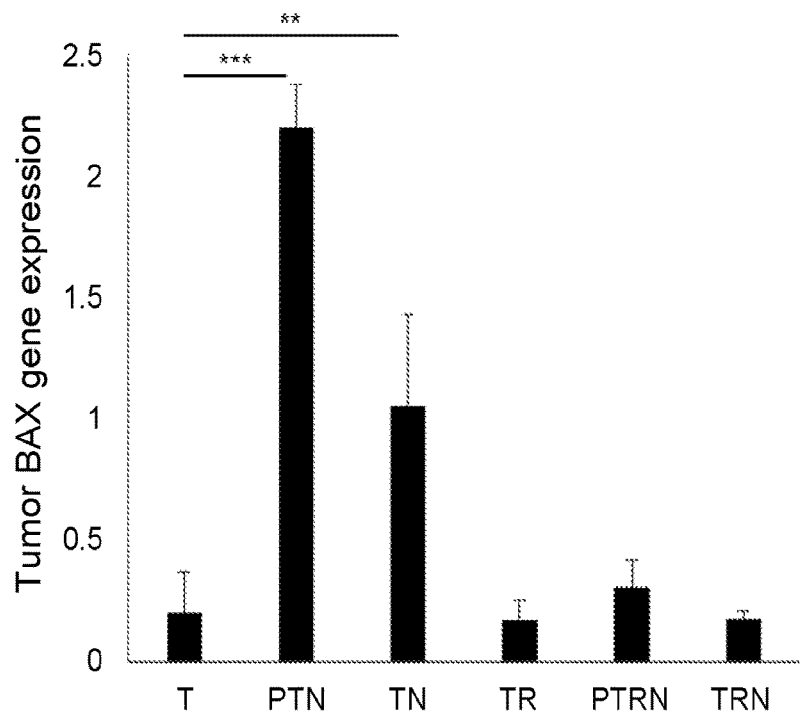
FIG. 1.

The inventive subject matter provides compositions and methods in which a nutritional supplement is provided that has the effect of both reducing inflammatory responses that are dysregulated in COVID-19 and in modulating apoptic pathways that are disrupted by SARS-CoV-2 infection of cells. The combined effect is believed to be highly beneficial in the treatment of COVID-19 by: (1) reducing SARS-CoV-2 viral load through restoration of apoptic pathways in infected cells, and (2) reducing inflammatory response in COVID-19. The Inventor believes that this approach to treatment of viral infection is also applicable to other viruses in which apoptosis is disrupted in infected cells and/or a clinically significant inflammatory component is present in active disease (e.g. influenza, HIV, etc.).

It should be appreciated that such treatment of viral infections can be treatment of an active viral infection. Such an active viral infection can be symptomatic, or in some embodiments can be an asymptomatic infection. Alternatively, in some embodiments treatment of a viral infection can be preventative or prophylactic. In such embodiments treatment with a nutritional supplement of the inventive concept can be effective to prevent active viral infection (e.g., through enhancing effective apoptosis of cells during initial exposure to a pathogenic virus).

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The Inventor has developed a nutritional supplement based upon high doses of fish oil and selenium, in addition to other supportive and nutritive components. An example of such a formulation is shown in Table 1. The selenium is preferably provided as selenium yeast or components thereof (such as peptides and/or amino acids prepared from selenium yeast). As such effects found in fish oil and selenium yeast studies can be extended to the use of this nutritional supplement. This formulation is well tolerated and has been found to have a high level of acceptance.

TABLE 1

| Component | Minimum | Maximum | Unit |
| --- | --- | --- | --- |
| Maltodextrin | 10000 | 50000 | mg |
| Whey Protein Isolate | 5000 | 60000 | mg |
| Whey Protein Concentrate | 1000 | 50000 | mg |
| Fructooligosaccharides/Inulin | 40 | 15000 | mg |
| Granulated Honey | 1000 | 9000 | mg |
| Oat Fiber | 500 | 15000 | mg |
| Natural French Vanilla Flavor | 500 | 20000 | mg |
| Soy Protein | 500 | 50000 | mg |
| Brownulated Powdered Brown Sugar | 500 | 10000 | mg |
| Natural Vanilla Masking Flavor | 500 | 5000 | mg |
| Lecithin | 200 | 10000 | mg |
| Milk, Non-fat | 50 | 5000 | mg |
| Rice Protein Powder | 50 | 5000 | mg |
| Calcium Caseinate | 50 | 2000 | mg |
| Oils | | | |
| Flax Seed Oil | 100 | 7000 | mg |
| Canola Oil | 100 | 7000 | mg |
| Borage Oil | 100 | 7000 | mg |
| Olive Oil | 100 | 7000 | mg |
| Fish Oil | 150 | 20,000 | mg |
| Pure Lemon Oil | 100 | 1000 | mg |
| Pure Orange Oil | 50 | 1000 | mg |
| Mixed Tocopherols | 0.5 | 200 | mg |
| Vitamins/Minerals | | | |
| Potassium Phosphate | 200 | 1500 | mg |
| Calcium Carbonate | 100 | 5000 | mg |
| Choline Bitartrate | 150 | 2500 | mg |
| Sodium Chloride | 100 | 2000 | mg |
| Calcium Phosphate Tribasic | 100 | 2000 | mg |
| Ascorbic Acid | 50 | 3000 | mg |
| Potassium Chloride | 50 | 2000 | mg |
| Magnesium Oxide | 50 | 500 | mg |
| Selenium (Yeast) | 30 | 10,000 | mcg |
| Chromium (Yeast) | 30 | 3000 | mcg |
| Molybdenum (Yeast) | 30 | 2000 | mcg |
| Inositol | 10 | 5000 | mg |
| Zinc Sulfate Monohydrate | 5 | 200 | mg |
| Dry Vitamin E Acetate | 5 | 2000 | IU |
| Niacinamide | 5 | 500 | mg |
| Ferric Orthophosphate | 3 | 100 | mg |
| Calcium Pantothenate | 3 | 200 | mg |
| Manganese Sulfate Monohydrate | 3 | 100 | mg |
| Beta Carotene | 1 | 100 | mg |
| Copper Gluconate | 1 | 15 | mg |
| Vitamin D3 | 25 | 5000 | IU |
| Vitamin K2 | 2 | 1000 | mcg |
| Pyridoxine HCl | 0.5 | 200 | mg |
| Potassium Iodide | 0.5 | 1500 | mg |
| Riboflavin | 0.5 | 1000 | mg |
| Thiamine Hydrochloride | 0.5 | 2500 | mg |
| Dry Vitamin K1 | 1 | 500 | mcg |
| Vitamin A Acetate | 500 | 100000 | IU |
| Folic Acid | 100 | 10000 | mcg |
| d-Biotin | 10 | 10000 | mcg |
| Vitamin B12 | 1 | 3000 | mcg |
| Amino Acids | | | |
| L-Carnitine | 300 | 30000 | mg |
| L-Glutamine | 500 | 60000 | mg |
| L-Arginine Base | 500 | 30000 | mg |
| Taurine | 50 | 2000 | mg |
| L-Lysine | 50 | 2000 | mg |
| Alpha Lipoic Acid | 10 | 1000 | mg |
| Resveratrol | 15 | 1500 | mg |
| Co-Enzyme Q10 | 10 | 5000 | mg |
| Glycine | 5 | 1000 | mg |
| Proline | 5 | 1000 | mg |
| Bacterial Cultures | | | |
| Lact. Acidophilus (app. 10 billion total) | 2 | 500 | mg |
| Bifido Bifidium (app. 10 billion total) | 2 | 500 | mg |
| Lac. Bulgaricus (app. 10 billion total) | 2 | 500 | mg |
| Bifido Longum (app. 10 billion total) | 2 | 500 | mg |
| Strep. Thermophilus (app. 10 billion total) | 2 | 500 | mg |
| Enzymes | | | |
| Papain | 5 | 100 | mg |
| Pepsin | 5 | 100 | mg |
| Lipase | 5 | 100 | mg |
| Bromelain | 5 | 100 | mg |
| Pancreatin 4X | 0.5 | 100 | mg |
| Lactase | 1 | 100 | mg |
| Betaine HCl | 3 | 100 | mg |
| Plant Products | | | |
| Pineapple Juice Powder | 2 | 500 | mg |
| Papaya Fruit Powder | 2 | 500 | mg |
| Quercetin | 30 | 3000 | mg |
| EGCG | 25 | 600 | mg |
| OPC | 15 | 500 | mg |
| Anthocyanins | 15 | 5000 | mg |

TABLE 1-continued

| Component | Minimum | Maximum | Unit |
|---|---|---|---|
| Ellagic Acid | 10 | 300 | mg |
| Astaxanthin | 2 | 90 | mg |
| Fucoidan | 20 | 1500 | mg |
| Mushroom Preparation | | | |
| Cordyceps | 5 | 6000 | mg |
| Ganoderma Lucidum | 15 | 10000 | mg |
| Shiitake | 40 | 15000 | mg |
| Maitake | 30 | 15000 | mg |
| Turkey Tail | 30 | 15000 | mg |

In some embodiments one or more minerals (e.g. selenium, molybdenum, chromium) can be provided in the form of a yeast preparation and/or metal substituted amino acid. In preferred embodiments selenium, molybdenum, and/or chromium are provided in the form of selenium yeast, molybdenum yeast, and chromium yeast, respectively. In preferred embodiments the nutritional supplement includes at least three components as represented in Table 1, for example fish oil, selenium (e.g. in the form of selenium yeast), and coenzyme Q (e.g. 10 to 5,000 mg coenzyme Q10, 50 mg to 3,000 mg coenzyme Q10, or 200 mg to 1,500 mg coenzyme Q10). Such additional components provide supplementation of necessary vitamins, minerals, and amino acids at elevated levels. Other components (e.g. enzymes, lecithin) serve to aid in digestion and absorption of components of the composition when consumed. The combination of these complementary activities provides a synergistic effect that exceeds the simple additive effect of individual components. It should be appreciated that the composition shown in Table 1 also includes certain flavorants (e.g. brown sugar, honey, vanilla flavor and masking agent) that serve to improve palatability and acceptance. Certain components (e.g. honey, brown sugar, milk, rice protein, casein) can provide both flavor and caloric energy. The Inventor has found that the combination of flavorants described above is effective in providing compliance with consumption of the nutritional supplement in effective amounts. In some embodiments, such flavorants can be excluded without negatively impacting the effectiveness of the nutritional supplement.

Components shown in Table 1 can be provided as a single formulation (for example, as a pill, tablet, capsule, powder, liquid, suspension, etc.) or can be segregated into different formulations (for example, as pills, tablets, capsules, powders, liquids, suspensions, or combinations thereof). The amounts shown in Table 1 are exemplary, and represent typical daily dosages provided to an adult of normal stature and otherwise normal health. These amounts can be adjusted to account for differences in body mass, gender, medical condition, etc. For example, a relatively small patient weighing 40 kilos or less may receive benefit from dosages provided at or below the low end of the ranges provided, whereas a relatively large patient weighing 100 kilograms or more may require dosages provided at the high end of the ranges noted (or more). In some embodiments such a daily dose can be distributed as multiple doses throughout the day. In some of such embodiments the composition of each of such distributed doses can be identical. In other embodiments the composition of such distributed doses can be different, provided the summation of such doses provides the required supplementation.

As shown in copending patent applications, the Inventor has demonstrated that such a nutritional composition can be used effectively in the treatment of cancer, particularly in combination with conventional therapies. In some embodiments a synergistic effect is found in such combination therapies. Within the context of this application, a synergistic effect is one in which the effect of combination therapy exceeds the summation of individual effects of monotherapies that comprise the combination therapy. In investigating the molecular basis of this phenomena, the Inventor has found that application of a supplement that includes fish oil and selenium had the effect of modulating markers associated with apoptosis as well as moderating inflammatory effects of these disease processes.

Inventor has noted that infection with viruses, in particular coronaviruses, can result in disruption of apoptic processes within the infected cells, and that pro-inflammatory 'cytokine storms' that can occur in infected individuals point towards dysregulation of the inflammatory process. On this basis the Inventor has concluded that tumor cells can, in certain aspects, serve as suitable model for elements of the viral infection process.

Without wishing to be bound by theory, the Inventor believes that a nutritional supplement that includes fish oil and selenium (for example, as shown above) has similar effects for correcting dysregulation of apoptosis in virus-infected cells and/or reducing inflammation that can accompany viral infections, where such viral infections result in dysregulation of apoptosis and/or inflammation (for example, due to pro-inflammatory cytokine expression or release). Examples of such viruses include coronaviruses (such as SARS-CoV-2), HIV, HCV, etc. It should be appreciated that one line of defense against viral infection is the induction of apoptosis in virus-infected cells. For example, Fung and Liu (Frontiers in Microbiology, vol. 5, June 2014) have shown that coronaviruses disrupt several cellular pathways that would otherwise move the coronavirus-infected cell towards programmed cell death, prolonging the cell's survival to generate and release more of the virus. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, Hanauske-Abel et al. (PLOS ONE, vol. 8, 2013) has shown that infection with HIV blocks apoptic pathways, and that restoration of these leads to apoptosis of HIV-infected cells.

Without wishing to be bound by theory the Inventor believes that application of a supplement that includes fish oil and selenium, which has been shown to be effective in modulating apoptosis markers in cancer cells, is effective in correcting the dysregulation of apoptosis associated with infection by certain viruses. Such viruses included, but are not limited to, SARS-CoV-2 (such as in COVID-19), HIV, and HCV. In addition, since such supplements have been demonstrated to be effective in reducing inflammation the Inventor believes that they do so in inflammation that results from such viral infections.

Figure 2:
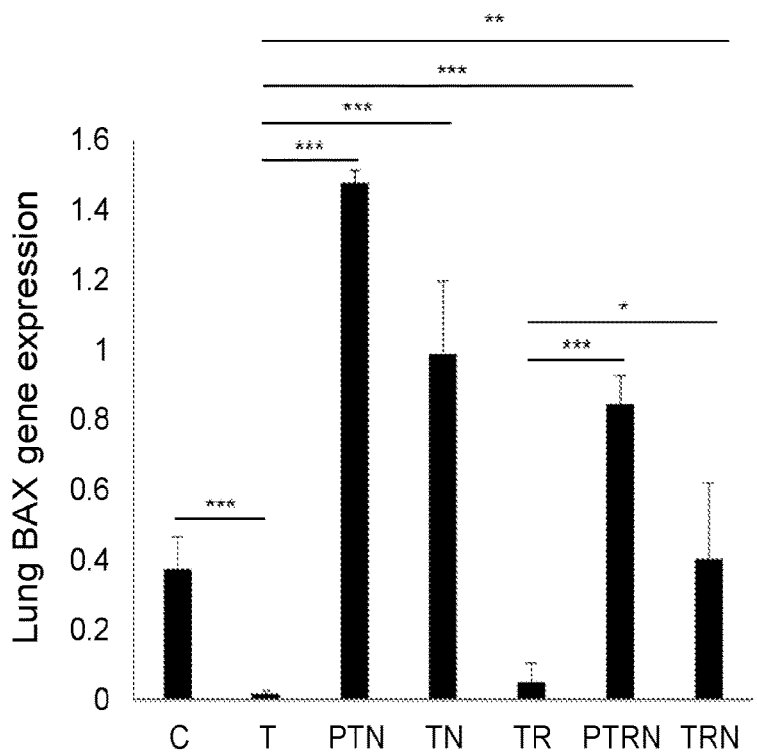
FIG. 2.

FIGS. 1 and 2 show the effects of treatment with a nutritional supplement containing fish oil and selenium on BAX expression cells that show reduced apoptic activity (T), in this instance, primary tumor BAX expression and metastatic (lung) tumor BAX expression (respectively). BAX is considered a marker for apoptosis. Since apoptosis is also suppressed in cells infected with certain viruses (e.g., coronaviruses), the Inventor believes that this system is highly relevant in regard to viral infection. As shown, BAX expression in cells with low apoptic activity (i.e., untreated tumor cells, T) is low. Treatment with a nutritional supplement containing fish oil and selenium (PTN, TN) resulted in dramatic increases in BAX expression, and elevated BAX expression. Accordingly, Inventor believes that administration of a composition that includes fish oil and selenium (e.g., as in Table 1) can be effective in increasing BAX expression in cells infected with certain viruses (e.g. coronavirus, HIV, HCV, etc.) and act to correct suppression of apoptosis in such infected cells. Such correction of apoptosis can serve to reduce cell-to-cell transmission, reducing viral load and preventing or reducing the severity of viral illness.

Figure 3:
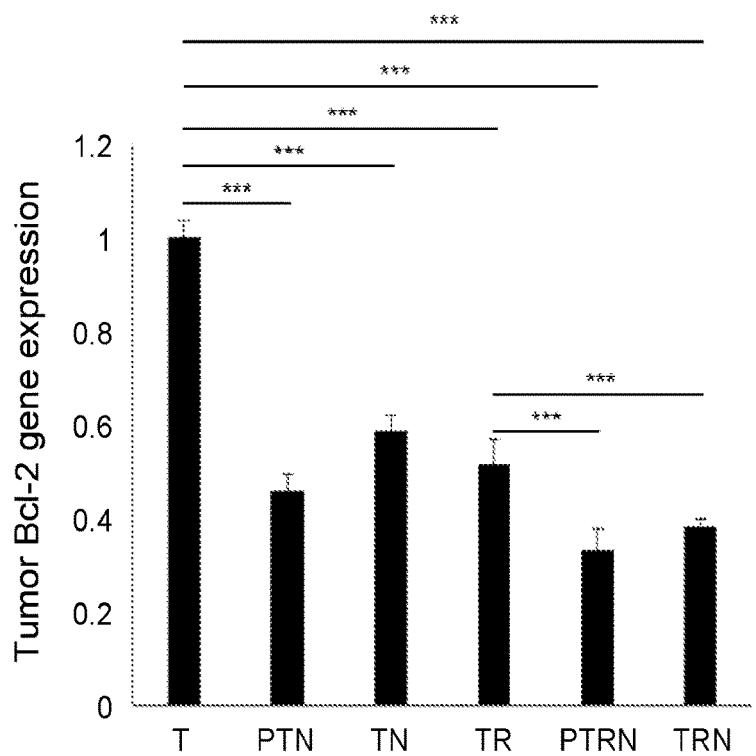
FIG. 3.
Figure 4:
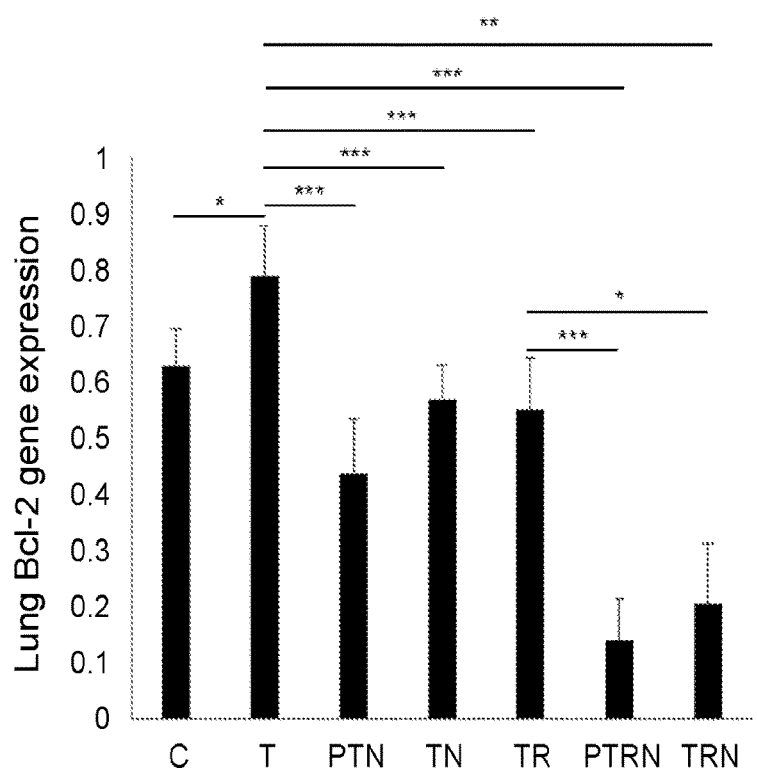
FIG. 4.

Bcl-2 is associated with a reduction in apoptosis. As shown in FIGS. 3 and 4, expression of Bcl-2 was found to be elevated in cells with low apoptotic activity (T), in this instance tumor cells and metastatic (lung) tumor cells (respectively). Expression of Bcl-2 was reduced by either treatment with a nutritional supplement containing fish oil and selenium (PTN. TN). Accordingly, Inventor believes that administration of a composition that includes fish oil and selenium (e.g., as in Table 1) can be effective in increasing BAX expression in cells infected with certain viruses (e.g. coronavirus, HIV, HCV, etc.) and act to correct suppression of apoptosis in such infected cells. Such correction of apoptosis can serve to reduce cell-to-cell transmission, reducing viral load and preventing or reducing the severity of viral illness.

Figure 5:
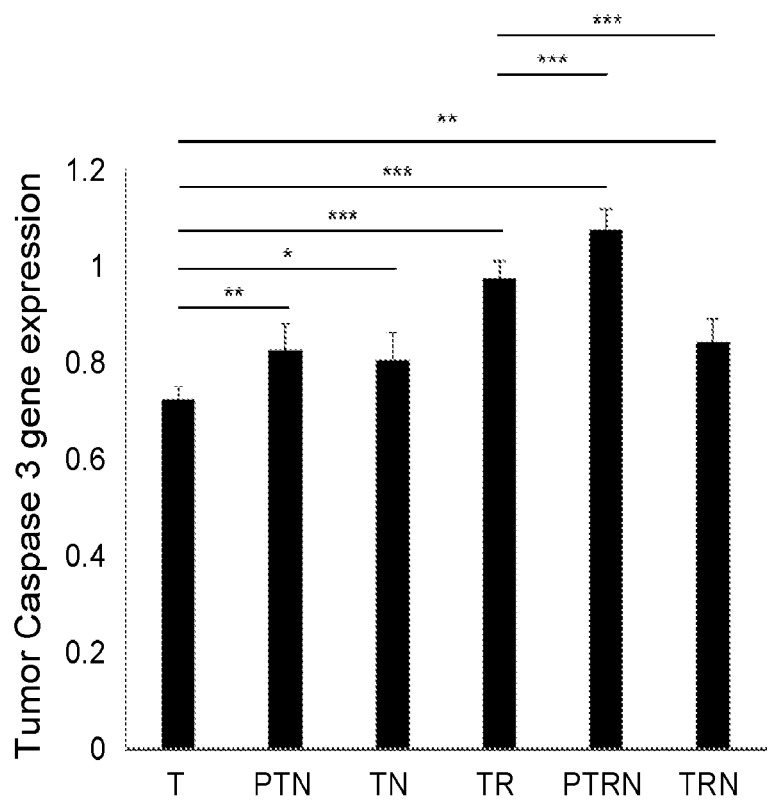
FIG. 5.

FIG. 5 shows the effects of treatment with a supplement containing selenium and fish oil on expression of caspase 3 in cells with reduced apoptosis, in this instance tumor cells (T). As shown in FIG. 5, expression of caspase 3 is reduced in such cells (T). Caspase 3 expression in such cells is increased by treatment with a nutritional supplement containing fish oil and selenium (TN, PTN). Accordingly, Inventor believes that administration of a composition that includes fish oil and selenium (e.g., as in Table 1) can be effective in increasing caspase-3 expression in cells infected with certain viruses (e.g. coronavirus, HIV, HCV, etc.) and act to correct suppression of apoptosis in such infected cells. Such correction of apoptosis can serve to reduce cell-to-cell transmission, reducing viral load and preventing or reducing the severity of viral illness.

Figure 6:
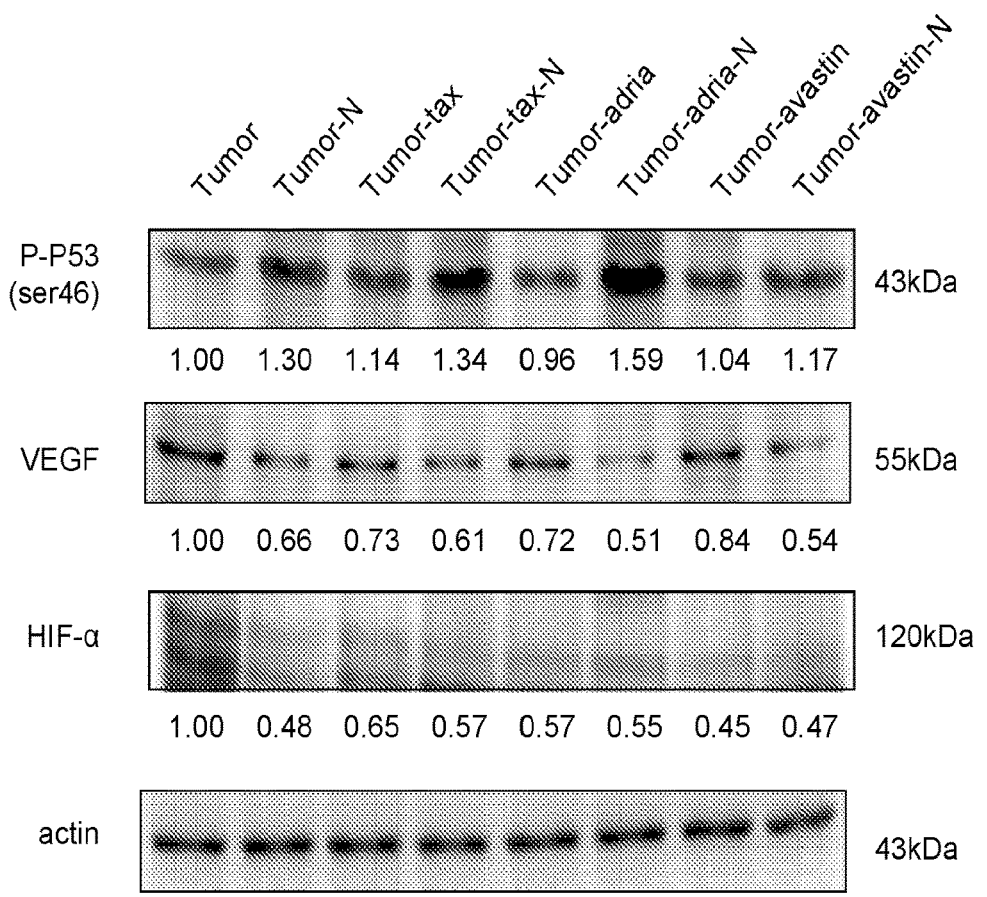
FIG. 6.
Figure 7:
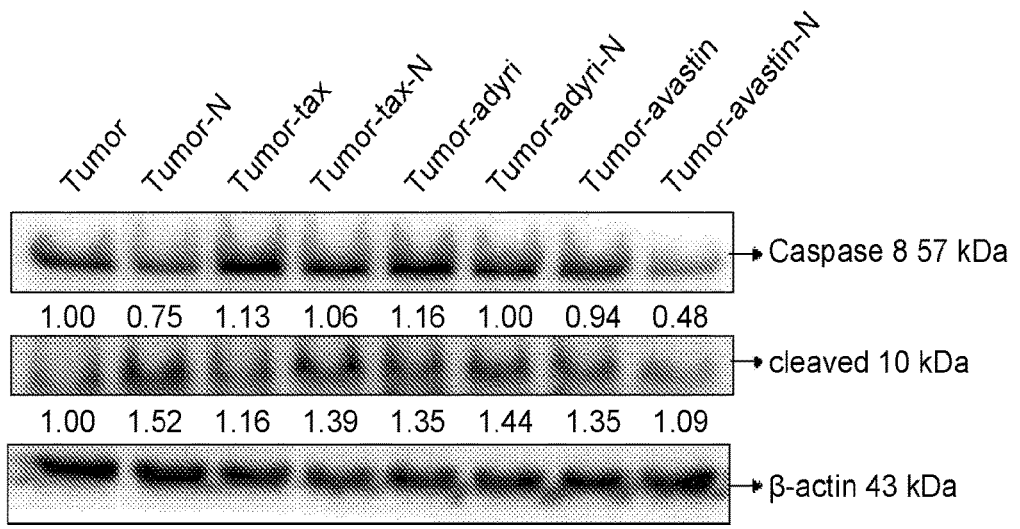
FIG. 7.
Figure 8:
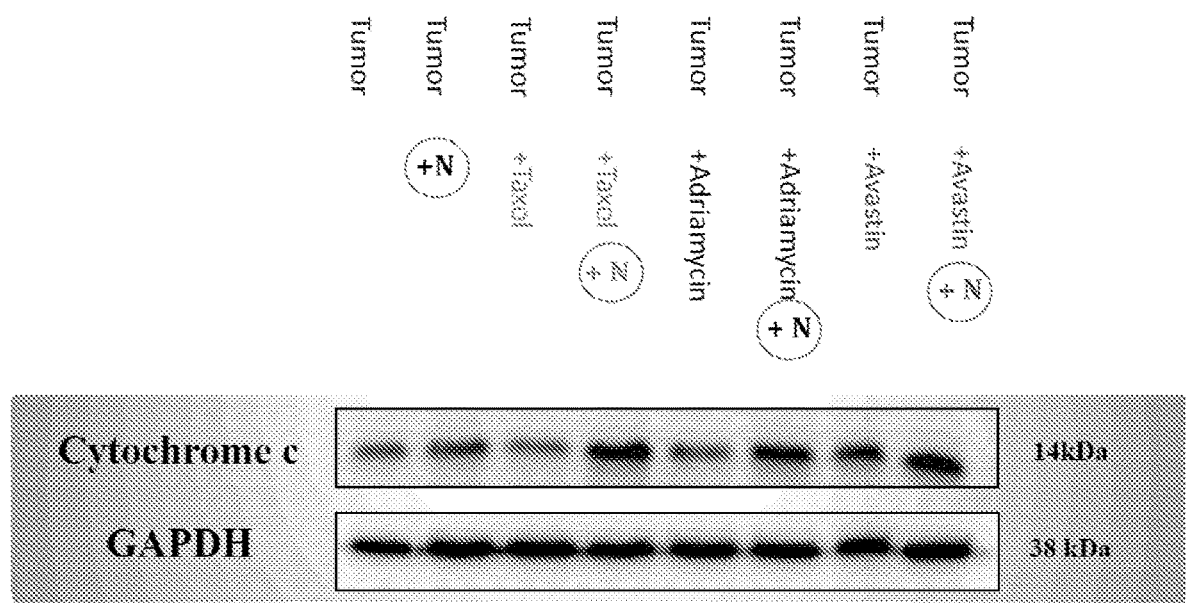
FIG. 8.

Table 2 shows typical results of qPCR studies for expression of apoptosis markers (Bax, Bcl-2, and caspase 3) in cells with low apoptosis activity, in this instance tumor cells.

suggest that therapy with a supplement containing fish oil and selenium modulate cell cycle phase distribution, which can in turn induce apoptosis and/or apoptic events in treated cells and/or cells of treated individuals. Inventors have found that nutritional supplements containing fish oil and selenium are effective in enhancing apoptosis in tumors in in vivo models for breast cancer, which the Inventor believes can serve as analogs of virus-infected cells. For example, FIG. 6 shows the expression of certain apoptosis markers (p53, VEGF, HIF-α) on tumor cells and the effect of use of such a nutritional supplement (N), certain small therapeutic molecules (avastin, taxol, adriamycin), and combination therapy on expression of apoptosis markers (specifically VEGF, p53, and HIF-α) in advanced tumors in mouse injected with breast cancer cells. As shown, the use of the nutritional supplement increases the expression of p53, while decreasing the expression of VEGF and HIF-α. Results from similar studies directed to Caspase 8 are shown in FIG. 7 FIG. 8 shows the effects treatment with a nutritional supplement containing fish oil and selenium ("N"), certain small molecule drugs (Taxol, Adriamycin, Avastin), and combined treatment on Cytochrome C expression in tumor cells that the Inventor believes can act as analogs or models of virus-infected cells. The Inventor believes that a nutritional supplement of the inventive concept can induce similar changes in virus infected cells, for example cells infected with a coronavirus, HIV, and/or HCV, thereby facilitating apoptosis of such infected cells.

Figure 9:
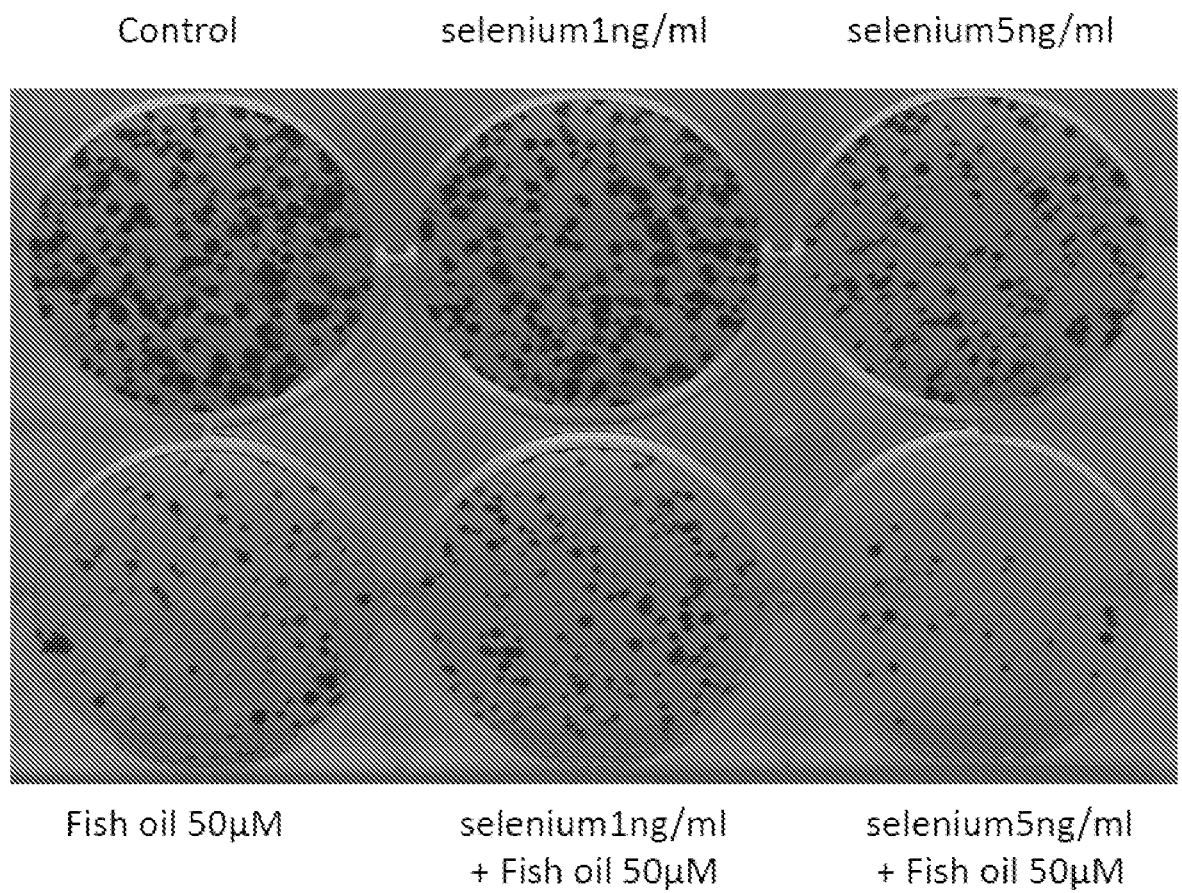
FIG. 9.
Figure 10:
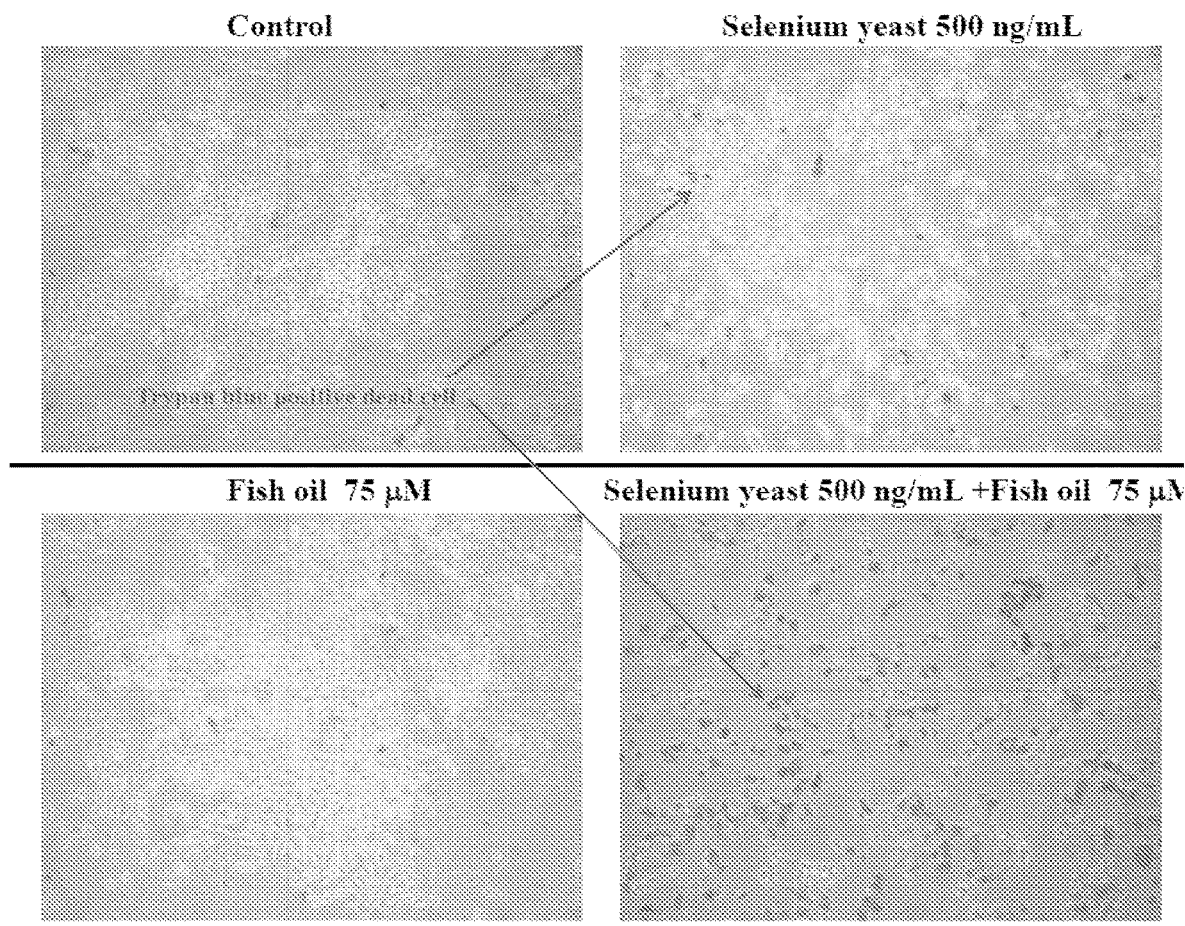
FIG. 10.

In addition to biochemical markers of apoptosis, apoptic effects can be observed directly in tumor cells, which the Inventor believes can act as analogs for virus-infected cells. For example, as shown in FIG. 9, growth of A549 cells in culture is slightly impacted by exposure to a supplement containing selenium or a supplement containing fish oil, but is dramatically impacted by a supplement containing both fish oil and selenium. Similarly, trypan blue staining of A549 cells in culture show only slight effects in inducing cell death when exposed to a supplement containing selenium or a supplement containing fish oil, but shows a dramatic increase in cell death when exposed to a supplement containing both fish oil and selenium, as shown in FIG. 10. The Inventor believes that a nutritional supplement of the inventive concept can induce similar effects on growth and induction of cell death in virus infected cells, for example cells infected with a coronavirus, HIV, and/or HCV.

TABLE 2

|     | Bax | Bcl-2 | Bax/Bcl-2 | caspase 3 |
| --- | --- | --- | --- | --- |
| T   | 0.31 ± 0.00 | 1.41 ± 0.67 | 0.22 ± 0.12 | 1.03 ± 0.88 |
| TN  | 5199.29 ± 2321.78 | 241.89 ± 7.44 | 21.49 ± 10.19 | 47708.35 ± 7808.87 |
| TR  | 1.09 ± 1.39 | 0.99 ± 0.16 | 1.10 ± 0.03 | 0.71 ± 0.06 |
| TRN | 7858.24 ± 1593.75 | 213.40 ± 8.45 | 36.82 ± 9.56 | 46977.1 ± 5263.41 |

As shown, the Bax/Bcl-2 expression ratio is low in cells with low apoptosis activity (T). Surprisingly, treatment with a nutritional supplement containing fish oil and selenium (TN, PTN) provided a significant increase in this ratio, indicating an increase in apoptosis. Caspase 3 was dramatically increased by treatment with a nutritional supplement containing fish oil and selenium, The Inventor believes that a nutritional supplement of the inventive concept can induce similar changes in virus infected cells, for example cells infected with a coronavirus, HIV, and/or HCV, thereby increasing apoptosis in infected cells.

Apoptosis and/or apoptic events are associated with certain cell cycle phases. Studies of cell cycle phase distribution Viral infection can also result in inflammation, which can be characterized by the presence of pro-inflammatory cytokines in serum. Some viruses (notably, coronaviruses) are known to induce a so-called "cytokine storm", which can lead overwhelming shock and, in some instances, to death. Moderation of the body's defensive inflammatory response is a key component in treatment of such viral infections Inflammatory responses, such as those mediated by pro-inflammatory cytokines are also found in animals carrying tumors. Accordingly, the Applicant believes that such animals can act as models for inflammatory conditions (including those induced by viral infection).

Inflammation is mediated, at least in part, by elaboration of pro-inflammatory cytokines. The Inventor has noted that elevated levels of such cytokines are also found with some tumors. Without wishing to be bound by theory, the Inventor believes that therapies effective to modulate the inflammatory response (e.g., reduction in pro-inflammatory cytokines and/or increase in anti-inflammatory cytokines) in such a condition can be useful in moderating the inflammatory response in individuals with certain viral infections (e.g. coronaviruses, HCV, HIV, etc.).

Figure 11:
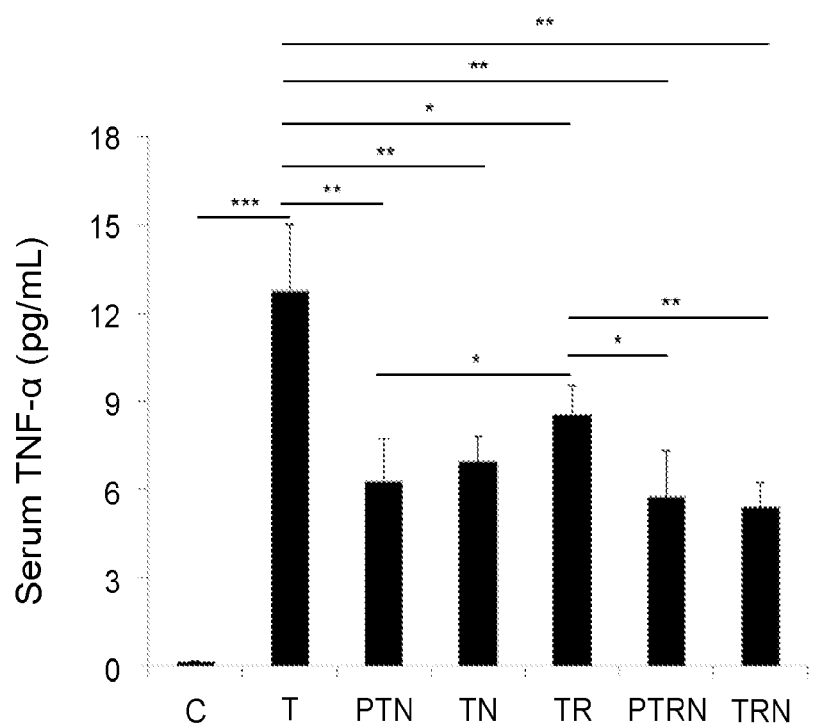
FIG. 11.
Figure 12:
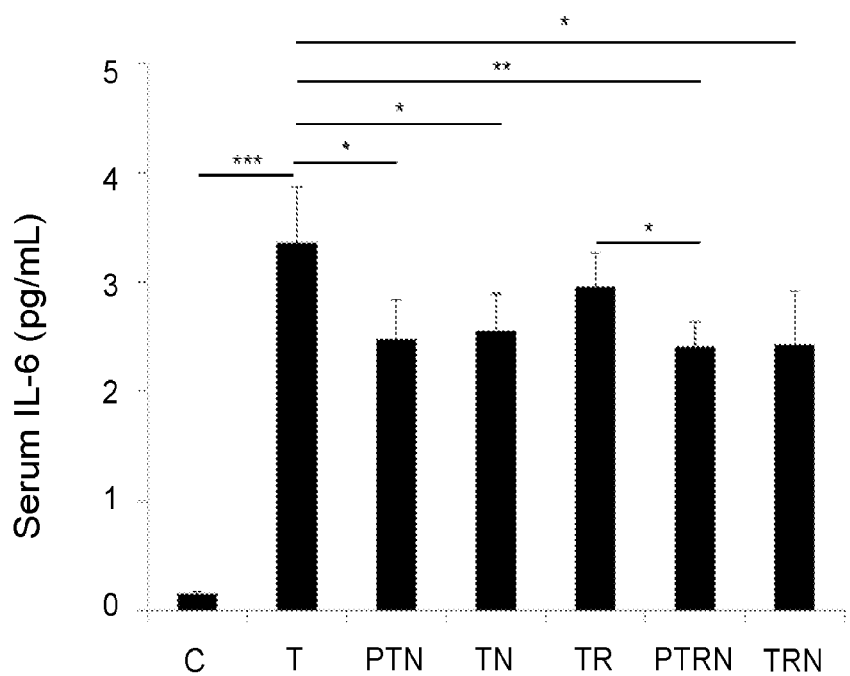
FIG. 12.

FIGS. 11 and 12 show the effect of administration of a nutritional supplement containing fish oil and selenium on the concentration of pro-inflammatory cytokines in mice carrying tumors. FIG. 11 shows values for serum TNF-α, a pro-inflammatory cytokine. It is apparent that untreated tumor bearing animals (T) show highly elevated concentrations of TNF-α, a pro-inflammatory cytokine. Treatment with a nutritional supplement containing fish oil and selenium (TN, TPN) resulted in a reduction in serum TNF-α, indicating a reduction in inflammation. The Inventor believes that treatment with a nutritional supplement that includes selenium and fish oil can similarly reduce inflammation in individuals with a viral infection (e.g., with coronavirus, HCV, HIV, etc.), and reduce the occurrence or severity of said inflammation-particularly inflammation leading to the development of a cytokine storm.

FIG. 12 shows the results of similar studies where the serum concentration of IL-6, which has pro-inflammatory activities, was characterized. As shown, untreated animals (T) show elevated levels of IL-6. Treatment of animals with a nutritional supplement that includes selenium and fish oil (TN, PTN) shows a reduction in serum IL-6, indicating a reduction in inflammation. The Inventor believes that a nutritional supplement of the inventive concept can induce similar changes in viral infections, for example with a coronavirus, HIV, and/or HCV. The Inventor believes that treatment with a nutritional supplement that includes selenium and fish oil can similarly reduce inflammation in individuals with a viral infection (e.g., with coronavirus, HCV, HIV, etc.), and reduce the occurrence or severity of said inflammation-particularly inflammation leading to the development of a cytokine storm.

Figure 13:
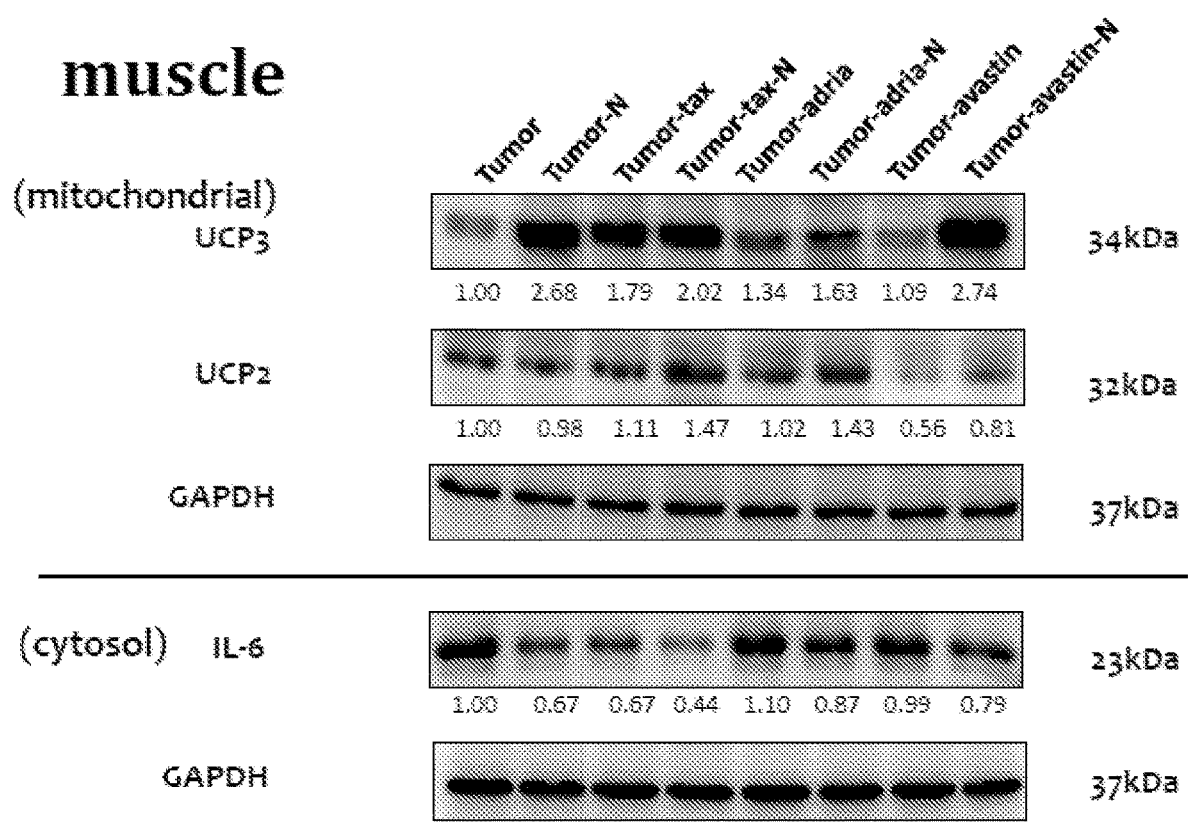
FIG. 13.

Reduction in inflammation associated markers on treatment with a nutritional supplement that includes fish oil and selenium is also evident on a molecular level. The Inventor has observed that use of such a nutritional supplement is effective in preventing or reversing changes in the expression of specific biochemical markers associated with inflammation. This is also apparent at the molecular level, as shown in FIG. 13. FIG. 13 shows expression of muscle-related proteins found in mitochondria and associated with inflammation (UCP3, UCP2) and an inflammation-related cytokine in cytosol (IL6). The Inventor believes that a nutritional supplement of the inventive concept can induce similar changes in infection with a virus, such as with a coronavirus, HIV, and/or HCV.

Figure 14:
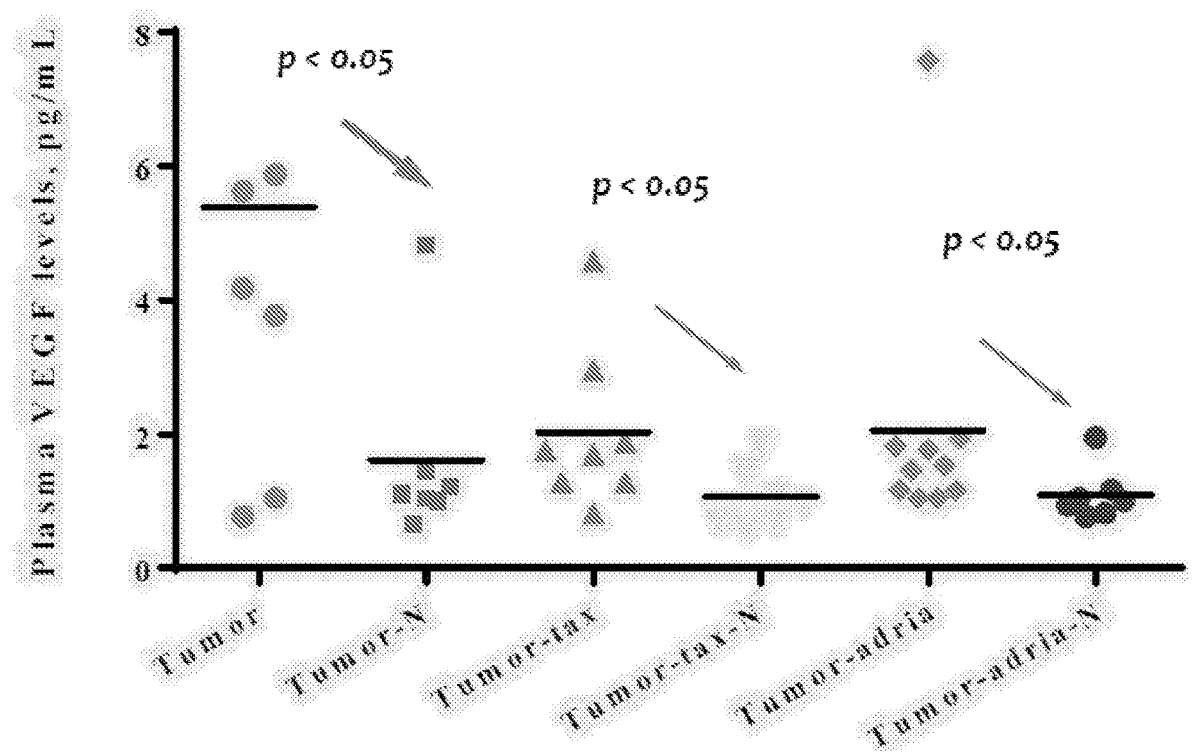
FIG. 14.
Figure 15:
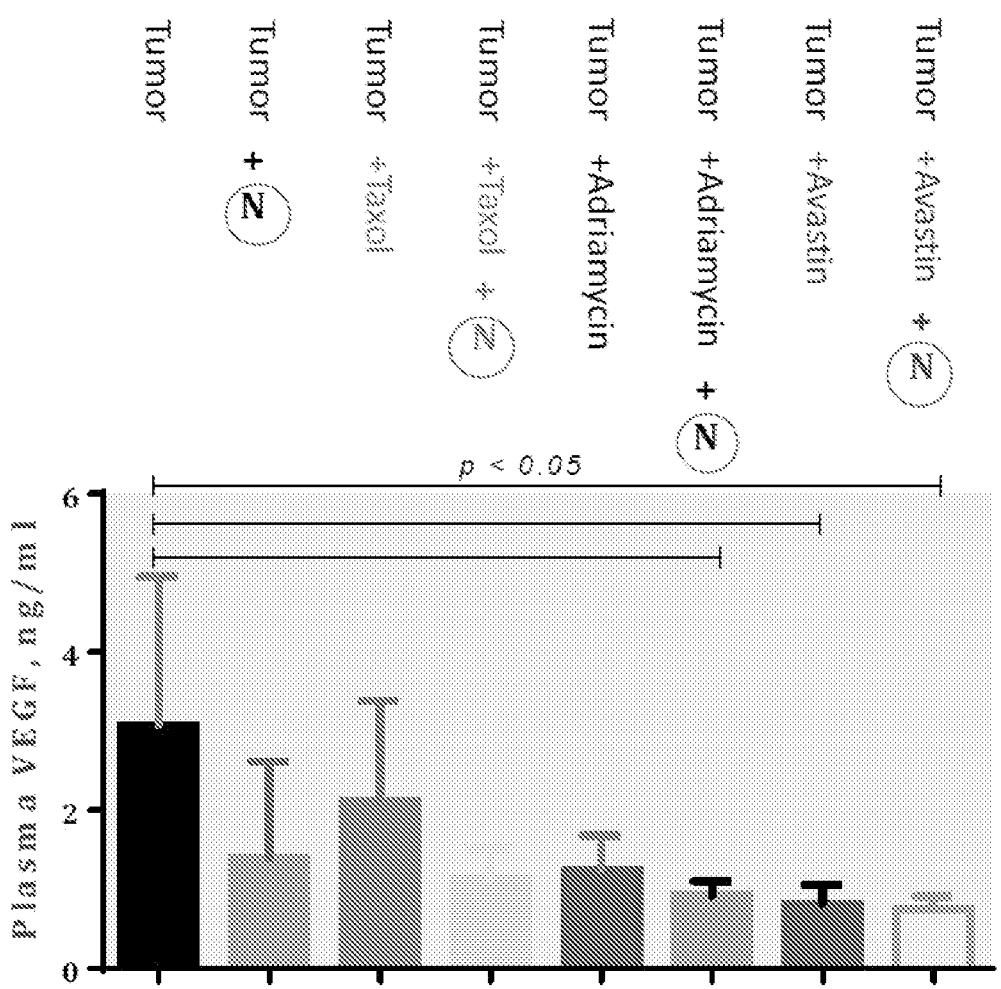
FIG. 15.

VEGF has been associated with an increase in vascularization during inflammatory processes, and contributes to COVID-19 related inflammation. Surprisingly, the Inventor has found that a nutritional supplement that includes fish oil and selenium can modulate levels of VEGF. As shown in FIG. 14 use of such a nutritional supplement (N), either alone or in combination with certain small molecule drugs (Taxol, or "tax", and Adriamycin, or "adria", in this example) in in vivo models of breast cancer (believed by the Inventor to serve as an analog of virus infected cells) was found to reduce plasma VEGF concentrations, indicating that it can provide an anti-inflammatory and anti-angiogenesis effect in viral infections (e.g., with a coronavirus, HCV, HIV, etc.). Similar results are seen with Avastin (see FIG. 15). The effect is seen with the supplement alone, and cotherapy with such a supplement enhances the VEGF-lowering effects of chemotherapeutic drugs.

Figure 16:
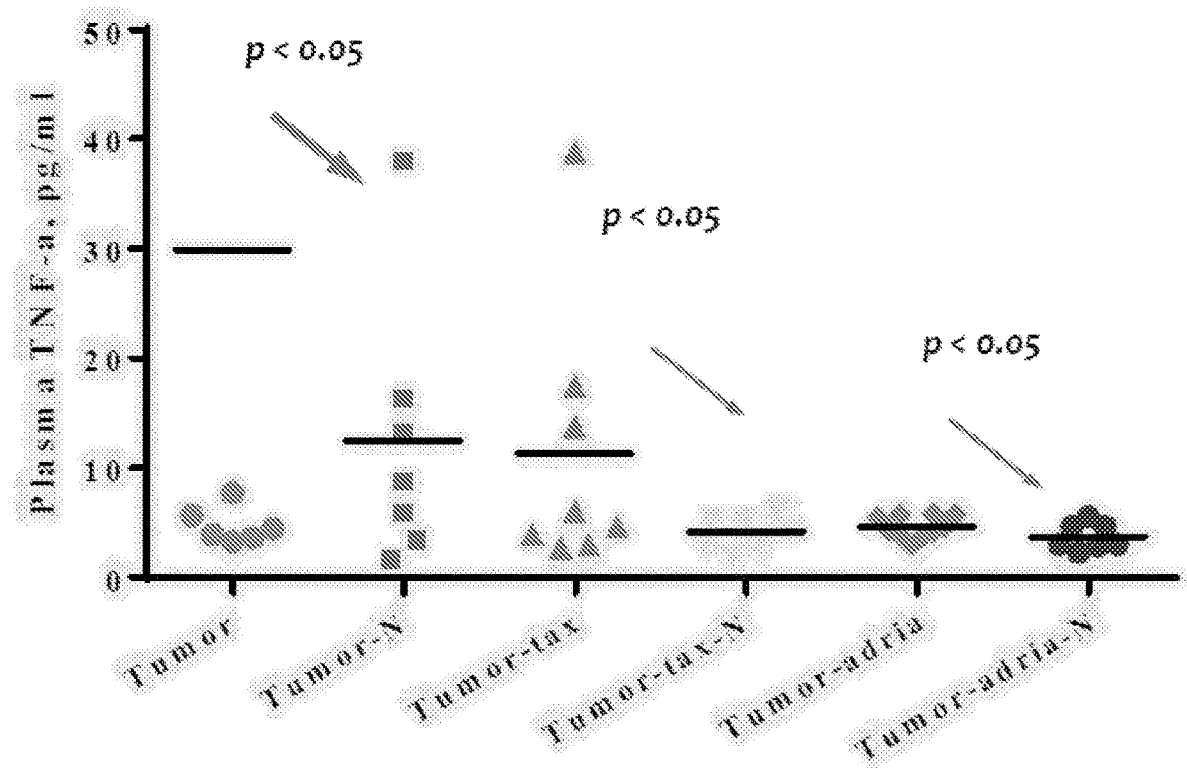
FIG. 16.
Figure 17:
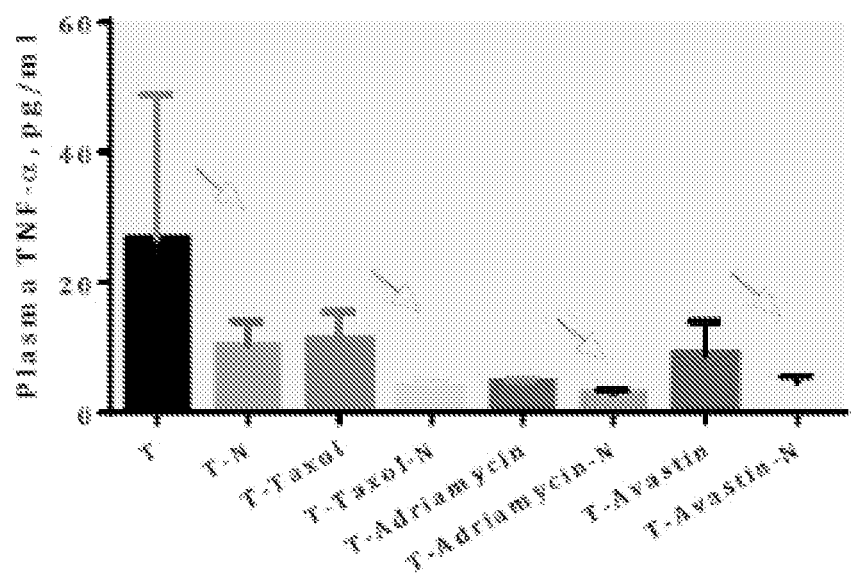
FIG. 17.
Figure 18:
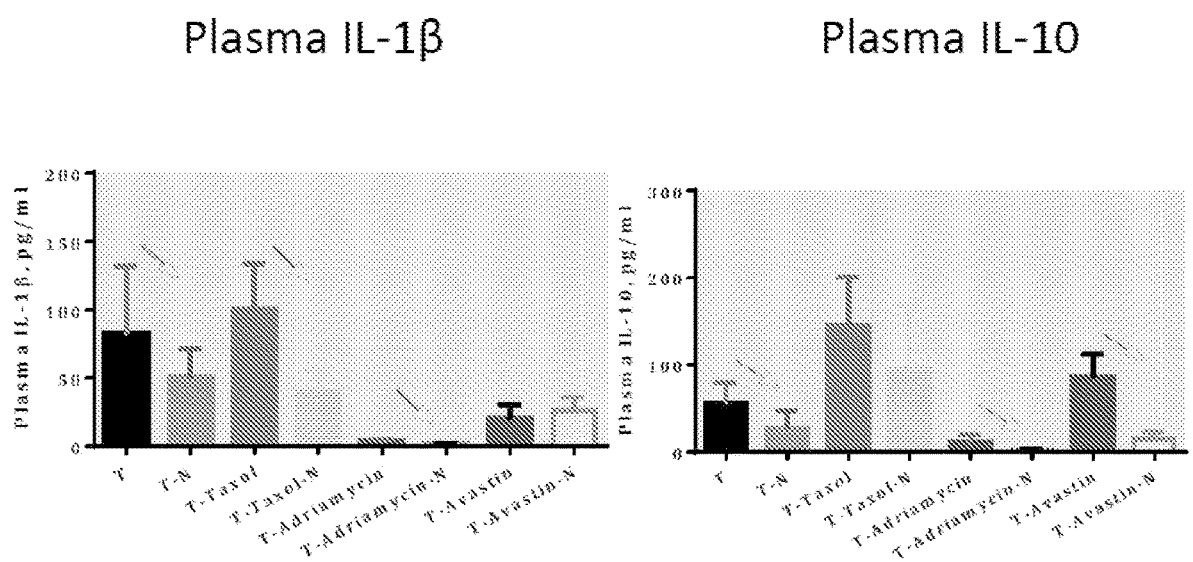
FIG. 18.
Figure 19:
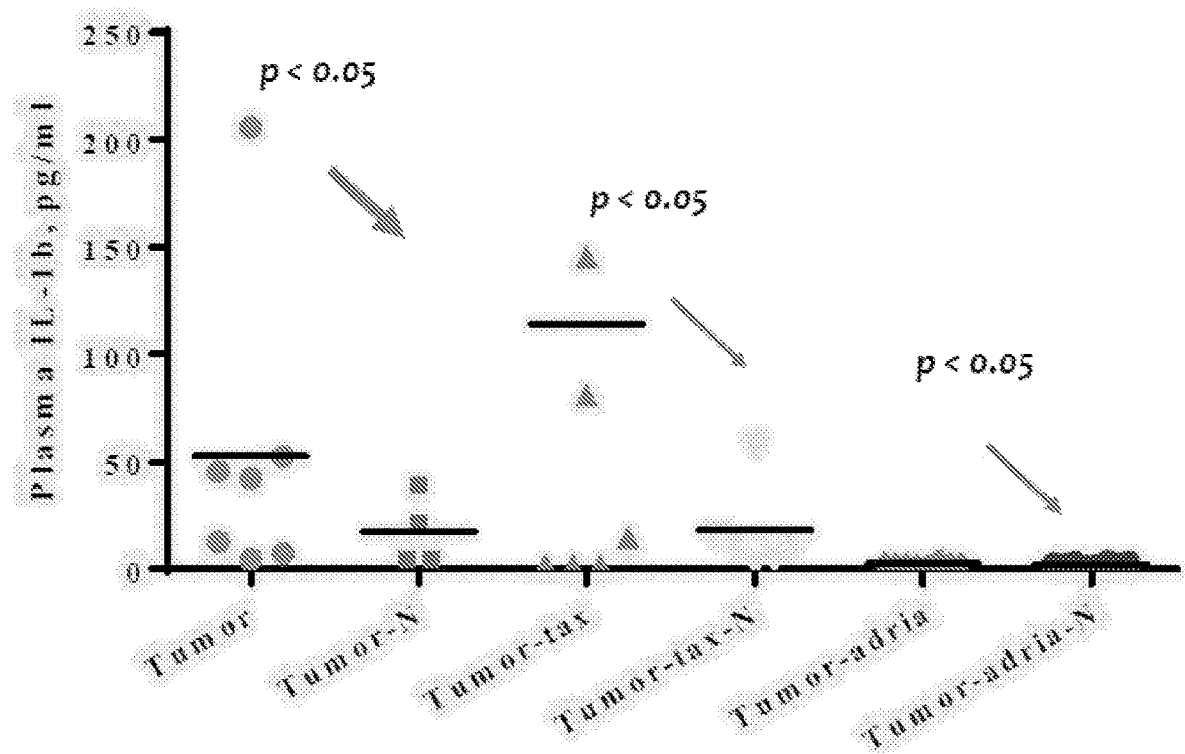
FIG. 19.

As shown in FIG. 16 and FIG. 17, similar effects are seen in the reduction of the pro-inflammatory cytokine TNF-α in an in vivo breast cancer model in treated animals (TN) vs untreated animals (T), which the Inventor believes can serve as an analog for viral infection. Similar effects are seen in the reduction of the pro-inflammatory cytokines IL1-β and IL-10 (see FIG. 18) in treated animals (TN) relative to untreated animals (T). Similarly, the effects of a nutritional supplement containing fish oil and selenium (N) in combination, both alone and in combination with certain small molecule drugs (taxol and adriamycin), on plasma IL-1β in an in vivo model of breast cancer is shown in FIG. 19. The Inventor believes that a nutritional supplement of the inventive concept can induce similar changes in infection with a virus, such as with a coronavirus, HIV, and/or HCV, thereby reducing inflammation and improving patient outcome in the case of such viral infections.

Figure 20:
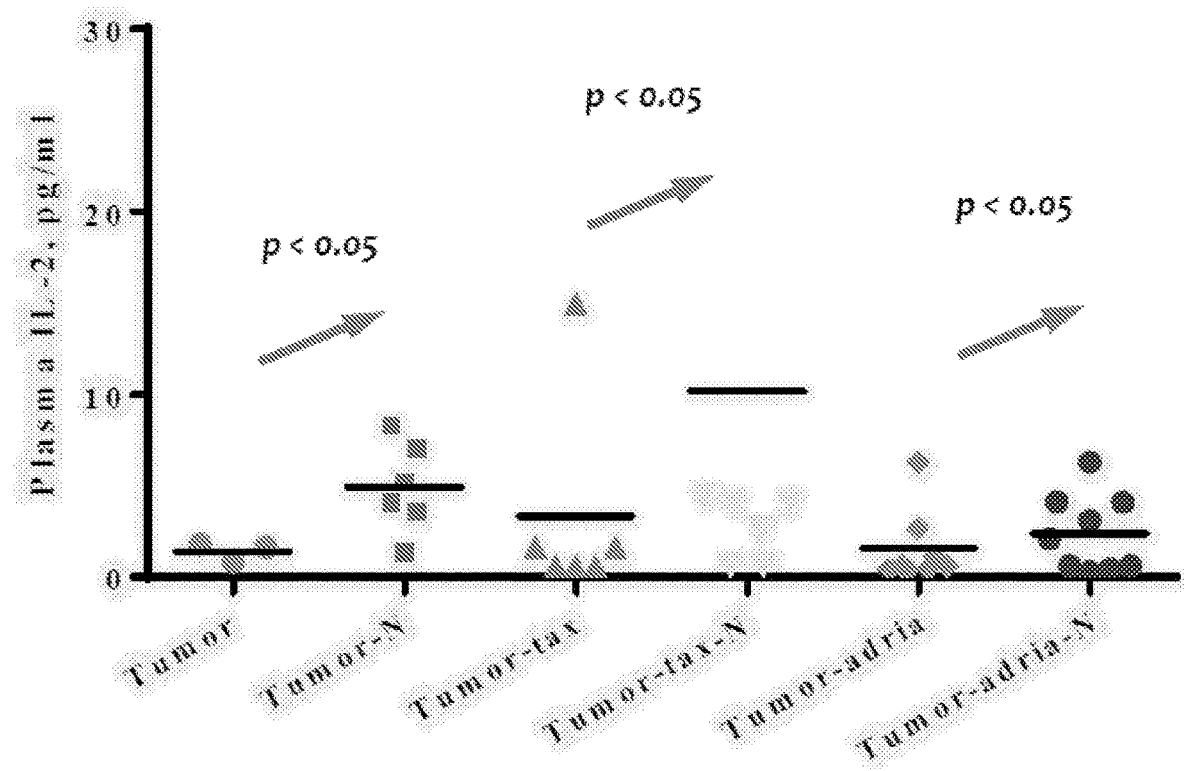
FIG. 20.
Figure 21:
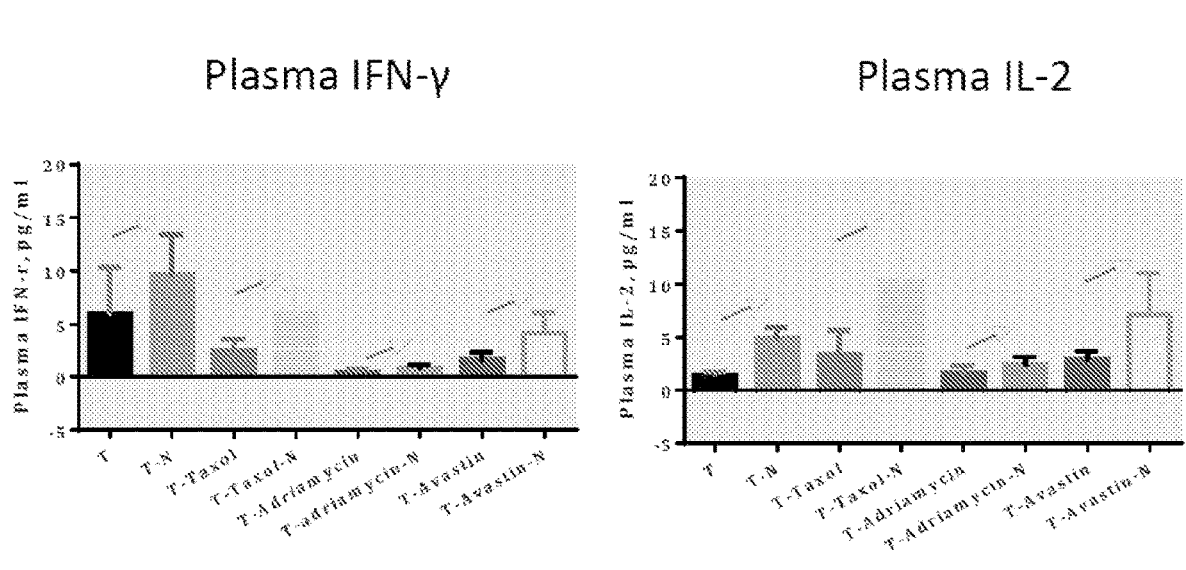
FIG. 21.

Conversely, the Inventor has found that the use a nutritional supplement containing fish oil and selenium can increase plasma concentrations of some cytokines, both in isolation and in combination with chemotherapeutic drugs. For example, as shown in FIG. 20 and FIG. 21 (right panel) plasma concentrations of IL2 are increased in an in vivo model of breast cancer show treated. It should be appreciated that IL2 is considered to be useful in proliferation of T cells and generation of effector and memory T cells that are important in the response to viral infection (e.g. COVID-19). IL2 is also recognized as important in the remission and recovery of patients with COVID-19. Plasma concentration of IFN-γ, another immune-activating cytokine, are also observed in such studies as shown in FIG. 21 (left panel). Notably, interferon therapy has been found to be useful for the treatment of a range of viral infections. The Inventor believes that a nutritional supplement of the inventive concept can induce similar changes infection with a virus, such as with a coronavirus, HIV, and/or HCV.

As noted above, the Inventor has found that treatment with fish oil and selenium (preferably in the form of selenium yeast) can effectively reduce inflammation and improve dysregulation of apoptosis, both of which are associated with infection by certain viruses (such as SARS coronaviruses, MERS coronaviruses, HCV, and HIV). Suitable treatment protocols can include treatment with a composition that includes fish oil to provide at least 1 g, 2 g, 3 g, 4 g, 5 g, 6 g, 7 g, 8 g, 9 g, 10 g, 12 g, 14 g, 16 g, 18 g, 20 g, 30 g, or 50 g of fish oil per day for a person of average size. Such fish oil can have an EPA:DHA ratio of about 3:2. Similarly, such a treatment protocol can include treatment with a composition that includes selenium (preferably in the form of selenium yeast) to provide at least 1 mg, 2 mg, 3 mg, 4 mg, 5 mg, 6 mg, 7 mg, 8 mg, 9 mg, 10 mg, 15 mg, 20 mg, 30 mg, 40 mg, or 50 mg per day for a person of average size. These amounts can be adjusted to accommodate for individuals of above average or below average size. Similarly, such amounts can be adjusted to accommodate the severity of viral infection (for example, being adjusted during the course of treatment).

Such doses of nutritional supplement containing selenium and fish oil can be provided on any suitable schedule. For example, a daily dose can be distributed throughout the day (e.g. from once an hour to every 12 hours), or can be provided as a single dose. In some embodiments such a dose of nutritional supplement can be administered daily, every two days, every three days, weekly, every two weeks, or at greater intervals. In some embodiments the duration of treatment can range from one day to ongoing, and can be limited to one week, two weeks, three weeks, one month, two months, three months, 6 months, a year, or greater than one year.

In some embodiments of the inventive concept one or more supplementary drug(s) useful in treating viral infections can be administered in combination with treatment with a nutritional supplement containing selenium and fish oil. For example, monoclonal antibodies directed to SARS-CoV-2, Remdesivir, corticosteroids (e.g., dexamethasone), IL-6 inhibitors, barictinib, and/or tocilizumab have been used to treat COVID19. Protease inhibitors and reverse transcriptase inhibitors have been used to treat HIV infection. Interferon, Ribavarin, Daclatasvir, Elbasvir, Grazoprevir, Glecaprevir, Pibrentasvir, Ombitasvir, Paritaprevir, Ritonavir, Dasabuvir, Simeprevir, Sofosbuvir, Velpatasvir, and Voxilaprevir have been used to treat HCV infection. In some embodiments one or more supplementary drug(s) can be provided on the same schedule as that of a nutritional supplement that includes selenium and fish oil. In other embodiments one or more supplementary drug(s) can provided on a different schedule than that of a nutritional supplement that includes selenium and fish oil. Such combined therapies can provide synergistic effects (i.e., greater than additive effects observed from treatment with individual components of the combined therapy) in treating viral disease.

The Inventor has noted that data during the generation of these studies indicates that application of radiotherapy can enhance the observed effects of treatment with a nutritional supplement fish oil and/or selenium. These in vivo studies utilized low doses of radiation, on the order of 2 rems or less. As shown in FIGS. 1 to 5 and FIGS. 11 and 12, combination therapy with such low level radiation in combination with a nutritional supplement that includes selenium and fish oil (TRN, PTRN) can enhance the effect seen with treatment using only the nutritional supplement, and can provide a synergistic effect (i.e., greater than the additive effects of treatment with radiation and the nutritional supplement individually). Accordingly, in some embodiments of the inventive concept fish oil and selenium are provided in combination with low dose (e.g. 2 rems or less) radiotherapy to treat viral infections. Based on data generated on the use of such nutritional supplements in combination with radiotherapy the Inventor believes that such radiotherapy can potentiate the effects of therapy with selenium and fish oil in reducing inflammation and correcting dysregulated apoptosis in individuals infected with viruses as detailed above. Such radiation can be provided prior to application of a suitable nutritional supplement, during application of the nutritional supplement, or after application of the nutritional supplement. Such radiotherapy can be applied once, or can be provided as a series of repeated applications. Frequency of repeated applications of the radiotherapy can be daily, on alternating days, every third day, twice a week, weekly, or every two weeks.

The Inventor has noted that data during the generation of these studies indicates that application of chemotherapy with small molecule drugs (e.g., taxol or "tax", adriamycin or "adria", avastin) used to treat cancer can enhance the observed effects of treatment with a nutritional supplement fish oil and/or selenium. As shown in FIGS. 6 to 8 and FIGS. 13 to 18, combination therapy with such a chemotherapy drug in combination with a nutritional supplement that includes selenium and fish oil can enhance the effect seen with treatment using only the nutritional supplement, and can provide a synergistic effect (i.e., greater than the additive effects of treatment with the chemotherapy drug and the nutritional supplement individually). The Inventor believes that such enhancement of the effects of a nutritional supplement that includes selenium and fish oil can be observed at doses of a chemotherapy drug that are lower than those utilized in cancer chemotherapy (e.g. 1%, 3%, 5%, 10% 20% 30% 40%, or 50% of the conventional dose), permitting their use with minimal to no side effects associated with cancer chemotherapy. Accordingly, in some embodiments of the inventive concept fish oil and selenium are provided in combination with a cancer chemotherapy drug to treat viral infections. Based on data generated on the use of such nutritional supplements in combination with chemotherapy the Inventor believes that cotherapy with one or more of such cancer chemotherapy drugs can potentiate the effects of therapy with selenium and fish oil in reducing inflammation and correcting dysregulation of inflammatory and/or apoptosis in individuals infected with viruses as detailed above. In such embodiments one or more chemotherapeutic drugs used in the treatment of cancer can be provided prior to application of a suitable nutritional supplement, during application of the nutritional supplement, or after application of the nutritional supplement. Such cotherapy with one or more chemotherapeutic drugs used in the treatment of cancer can be applied once, or can be provided as a series of repeated applications. Frequency of repeated cotherapy using one or more chemotherapeutic drugs used in the treatment of cancer can be daily, on alternating days, every third day, twice a week, weekly, or every two weeks It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of treating a viral infection, comprising:
    a) obtaining a nutritional supplement comprising therapeutically effective amounts of fish oil and yeast comprising selenium, and
    b) administering a therapeutically effective amount of the nutritional supplement to an individual in need of treatment for the viral infection to treat the viral infection or sequelae of the viral infection, wherein the viral infection results from infection with a virus that induces a dysregulation of apoptosis in a cell infected with the virus, and wherein the nutritional supplement provides fish oil and selenium in quantities sufficient to modify an apoptic event in the cell infected with the virus upon administration.

2. The method of claim 1, wherein amounts of fish oil and selenium are additionally selected to reduce serum concentration of a pro-inflammatory cytokine in the individual.

3. The method of claim 1, wherein selenium is provided at from 1,000 µg to 10,000 µg per day.

4. The method of claim 1, wherein fish oil is provided at from 1,000 mg to 20 mg per day.

5. The method of claim 1, wherein the nutritional supplement further comprises maltodextrin, 10,000 mg to 50,000 mg; whey protein isolate, 5,000 mg to 60,000 mg; whey protein concentrate, 1,000 mg to 50,000 mg; fructooligosaccharides and/or inulin, 40 mg to 15,000 mg; granulated honey, 1,000 mg to 9,000 mg; oat fiber, 500 mg to 15,000 mg; natural French Vanilla flavor, 500 mg to 20,000 mg; soy protein, 500 mg to 50,000 mg; powdered brown sugar, 500 mg to 10,000 mg; natural vanilla masking flavor, 500 mg to 5,000 mg; lecithin, 200 mg to 10,000 mg; milk, non-fat, 50 mg to 5,000 mg; rice protein powder, 50 mg to 5,000 mg; calcium caseinate, 50 mg to 2,000 mg; flax seed oil, 100 mg to 7,000 mg; canola oil, 100 mg to 7,000 mg; borage oil, 100 mg to 7,000 mg; olive oil, 100 mg to 7,000 mg; pure lemon oil, 100 mg to 1,000 mg; pure orange oil, 50 mg to 1,000 mg; mixed tocopherols, 0.5 mg to 200 mg; potassium phosphate, 200 mg to 1,500 mg; calcium carbonate, 100 mg to 5,000 mg; choline bitartrate, 150 mg to 2,500 mg; sodium chloride, 100 mg to 2,000 mg; calcium phosphate tribasic, 100 mg to 2,000 mg; ascorbic acid, 50 mg to 3,000 mg; potassium chloride, 50 mg to 2,000 mg; magnesium oxide, 50 mg to 500 mg; yeast comprising chromium in an amount of 30 pg to 3,000 ug; yeast comprising molybdenum in an amount of 30 ug to 2,000 ug; inositol, 10 mg to 5,000 mg; zinc sulfate monohydrate, 5 mg to 200 mg; dry vitamin E acetate, 5 IU to 2,000 IU; niacinamide, 5 mg to 500 mg; ferric orthophosphate, 3 mg to 100 mg; calcium pantothenate, 3 mg to 200 mg; manganese sulfate monohydrate, 3 mg to 100 mg; beta carotene, 1 mg to 100 mg; copper gluconate, 1 mg to 15 mg; vitamin D3, 25 IU to 5,000 IU; vitamin K2, 2 µg to 1,000 µg; pyridoxine HCl, 0.5 mg to 200 mg; potassium iodide, 0.5 mg to 1,500 mg; riboflavin, 0.5 mg to 1,000 mg; thiamine hydrochloride, 0.5 mg to 2,500 mg; dry vitamin K1, 1 µg to 500 ug; vitamin A acetate, 500 IU to 100,000 IU; folic acid, 100 µg to 10,000 µg; d-biotin, 10 pg to 10,000 µg; vitamin B12, 1 µg to 3,000 µg; L-carnitine, 300 mg to 30,000 mg; L-glutamine, 500 mg to 60,000 mg; L-arginine base, 500 mg to 30,000 mg; taurine, 50 mg to 2,000 mg; L-lysine, 50 mg to 2,000 mg; alpha lipoic acid, 10 mg to 1,000 mg; resveratrol, 15 mg to 1,500 mg; co-enzyme Q10, 10 mg to mg; glycine, 5 mg to 1,000 mg; proline, 5 mg to 1,000 mg; *Lactobacillus acidophilus* (app. 10 billion total), 2 mg to 500 mg; *Bifidobacterium bifidum* (app. billion total), 2 mg to 500 mg; *Lactobacillus bulgaricus* (app. 10 billion total), 2 mg to 500 mg; *Bifidobacterium longum* (app. 10 billion total), 2 mg to 500 mg; *Streptococcus thermophilus* (app. 10 billion total), 2 mg to 500 mg; papain, 5 mg to 100 mg; pepsin, 5 mg to 100 mg; lipase, 5 mg to 100 mg; bromelain, 5 mg to 100 mg; pancreatin, 0.5 mg to 100 mg; lactase, 1 mg to 100 mg; betaine HCl, 3 mg to 100 mg; pineapple juice powder, 2 mg to 500 mg; papaya fruit powder, 2 mg to 500 mg; quercetin, 30 mg to 3,000 mg; epigallocatechin gallate (EGCG), 25 mg to 600 mg; anthocyanins, 15 mg to 5,000 mg; ellagic acid, 10 mg to 300 mg; astaxanthin, 2 mg to 90 mg; fucoidan, 20 mg to 1,500 mg; *Cordyceps*, 5 mg to 6,000 mg; *Ganoderma lucidum*, 15 mg to 10,000 mg; Shiitake, 40 mg to 15,000 mg; Maitake, 30 mg to 15,000 mg; and Turkey Tail, 30 mg to 15,000 mg.

6. The method of claim 1, wherein the virus is a coronavirus.

7. The method of claim 6, wherein the coronavirus is SARS-CoV-2.

8. The method of claim 1, wherein the virus is HIV.

9. The method of claim 1, wherein the virus is hepatitis C virus (HCV).

10. The method of claim 1, wherein treatment comprises treatment of an active infection.

11. The method of claim 10, wherein the active infection is asymptomatic.

12. The method of claim 1, wherein treatment is prophylactic.

13. The method of claim 1, further comprising administering a therapeutically effective amount of radiotherapy.

14. The method of claim 13, wherein the radiotherapy comprises a nonzero radiation dose of up to 2 rems.

15. The method of claim 13, wherein the radiotherapy comprises a single application of radiation.

16. The method of claim 13, wherein the radiotherapy comprises a plurality of applications of radiation.

17. The method of claim 1, further comprising administering a therapeutically effective amount of a cancer chemotherapy drug.

18. The method of claim 17, wherein cancer chemotherapy drug is selected from the group consisting of a taxol, adriamycin, and avastin.

19. The method of claim 17, wherein the cancer chemotherapy drug is applied at a dose corresponding to from 1% to 50% of a dose of the cancer chemotherapy drug when administered for treatment of cancer.

* * * * *